United States Patent
Liu et al.

(10) Patent No.: US 12,415,100 B2
(45) Date of Patent: Sep. 16, 2025

(54) HEADBAND ASSEMBLY AND MASK SYSTEM

(71) Applicant: BMC MEDICAL CO., LTD., Beijing (CN)

(72) Inventors: Lina Liu, Beijing (CN); Mingzhao Zhou, Beijing (CN); Zhi Zhuang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 1066 days.

(21) Appl. No.: 17/263,579

(22) PCT Filed: Jul. 24, 2019

(86) PCT No.: PCT/CN2019/097504
§ 371 (c)(1),
(2) Date: Jan. 27, 2021

(87) PCT Pub. No.: WO2020/020229
PCT Pub. Date: Jan. 30, 2020

(65) Prior Publication Data
US 2021/0178199 A1   Jun. 17, 2021

(30) Foreign Application Priority Data
Jul. 27, 2018  (CN) .......................... 201810845624.1

(51) Int. Cl.
*A62B 18/08* (2006.01)
*A61M 16/06* (2006.01)
(52) U.S. Cl.
CPC ....... *A62B 18/084* (2013.01); *A61M 16/0605* (2014.02); *A61M 16/0683* (2013.01)
(58) Field of Classification Search
CPC ......... A62B 18/084; A62B 18/08; A62B 9/04; A62B 7/14; A61M 16/0605;
(Continued)

(56) References Cited

U.S. PATENT DOCUMENTS

| | | | | |
|---|---|---|---|---|
| 7,509,958 | B2 * | 3/2009 | Amarasinghe .... | A61M 16/0633 128/206.28 |
| 8,443,805 | B2 * | 5/2013 | Amarasinghe .... | A61M 16/0633 2/418 |

(Continued)

FOREIGN PATENT DOCUMENTS

| | | |
|---|---|---|
| CN | 101450239 A | 6/2009 |
| CN | 202538112 U | 11/2012 |

(Continued)

OTHER PUBLICATIONS

Machine Translation OFCN—104225751-A. Accessed from PE2E Search tool on Nov. 2023. (Year: 2014).*

*Primary Examiner* — Kendra D Carter
*Assistant Examiner* — Jaeick Jang
(74) *Attorney, Agent, or Firm* — Bayramoglu Law Offices LLC

(57) ABSTRACT

A headband assembly and a respiratory-mask system, wherein the headband assembly is of a planar structure in a spread and deployed state, and the headband assembly includes a head-mounting part (1) that is for clinging to and being worn on a head and connecting parts (2) that are connected to two sides of the head-mounting part (1) and are for connecting a respiratory mask; and the head-mounting part (1) includes an upper headband (11) that is for clinging to a top of the head and has a preset width and a rear headband (12) that is for clinging to a rear side of the head and is located under the upper headband (11), wherein the upper headband (11) is of an arch structure whose concave faces the rear headband (12). The headband assembly can cling to the head, to enable it to be firmly worn on the head.

9 Claims, 7 Drawing Sheets

(58) Field of Classification Search
CPC ...... A61M 16/0683; A61M 2205/0216; A61M 2207/00; A61M 16/06; A61M 16/0616; A61M 16/0633; A61M 16/0644; A61M 16/065; A61M 16/0655; A61M 16/0688; A61M 16/0694; B64D 11/00
See application file for complete search history.

(56) References Cited

U.S. PATENT DOCUMENTS

| | | | | |
|---|---|---|---|---|
| 10,576,234 B2* | 3/2020 | Brown | ............... | A61M 16/0683 |
| 2004/0083534 A1* | 5/2004 | Ruiz | ................ | A61M 16/0683 2/171.2 |
| 2007/0130663 A1 | 6/2007 | Lang et al. | | |
| 2009/0178680 A1* | 7/2009 | Chang | ............... | A61M 16/0683 128/207.11 |
| 2011/0072553 A1 | 3/2011 | Ho | | |
| 2011/0088700 A1* | 4/2011 | Ho | ........................ | A61M 16/06 128/207.11 |
| 2011/0253143 A1* | 10/2011 | Ho | .................... | A61M 16/0683 128/206.21 |
| 2018/0214655 A1* | 8/2018 | Kooij | ................. | A61M 16/0611 |

FOREIGN PATENT DOCUMENTS

| | | | |
|---|---|---|---|
| CN | 103945891 A | 7/2014 | |
| CN | 104225751 A * | 12/2014 | ........ A61M 16/0683 |
| CN | 204170254 U | 2/2015 | |
| CN | 204446892 U | 7/2015 | |
| CN | 109011084 A | 12/2018 | |
| CN | 209137670 U | 7/2019 | |
| DE | 102004037545 A1 | 2/2006 | |
| WO | 2004041341 A1 | 5/2004 | |
| WO | 2006072128 A1 | 7/2006 | |
| WO | 2008030831 A2 | 3/2008 | |
| WO | 2013076624 A1 | 5/2013 | |
| WO | 2017150990 A1 | 9/2017 | |

* cited by examiner

HEADBAND ASSEMBLY AND MASK SYSTEM

CROSS REFERENCE TO THE RELATED APPLICATIONS

This application is the national phase entry of International Application No. PCT/CN2019/097504, filed on Jul. 24, 2019, which is based upon and claims priority to Chinese Patent Application No. 201810845624.1, filed on Jul. 27, 2018, the entire contents of which are incorporated herein by reference.

TECHNICAL FIELD

The present application relates to the technical field of respiratory masks, and particularly relates to a headband assembly and a respiratory-mask system.

BACKGROUND

Respiratory-mask systems are worn on a face, and the respiratory-mask systems are positioned by using a headband assembly at a relatively comfortable position of the face, thereby ensuring the comfortableness of the wearing of the respiratory-mask system, to better realize the functions of conditioning, amelioration and treatment of the respiratory-mask system. Headband assemblies are the major component for connecting the respiratory-mask system and the human head, and because the heads of individuals differ greatly, headband assemblies are required to have a good comfortableness, a good conformability and enough adaptability. Accordingly, it can be seen that a proper structure of the headband assembly can enable most of the patients that wear a respiratory mask to obtain a usage state with excellent comfortableness and leakproofness.

The headband assembly that is mostly extensively used currently is of the "four-point type"; i.e., it is connected to the respiratory-mask system via four points, thereby realizing the comfortableness of the wearing of the respiratory-mask system. The "four-point-type" headband assemblies are generally "I-shaped" or "crown-shaped".

The "I-shaped" headband assembly is shown in FIG. 1. Such a headband assembly has a simple structure, and when deployed, all of its components can be placed in the same one plane. However, it has a low wearing firmness, the fixing position does not take into account the top of the head, and it generally can merely cooperate with a respiratory-mask system that has a forehead support, which results in a small quantity of the types of the respiratory-mask systems that can be adapted for.

The "crown-shaped" headband assembly is shown in FIG. 2. Such a headband assembly, as compared with the I-shaped headband, improves the wearing firmness, and provides the positioning at the top of the head of the wearer. Therefore, it may be used for respiratory-mask systems that have a forehead support and may also be used for respiratory-mask systems that do not have a forehead support. However, when such a headband assembly is deployed, generally all of its components cannot be placed in the same one plane (mainly, the part of the head-top band and the connecting parts cannot be placed in the same plane), its manufacturing process is complicated, which requires the support of massive clinical data of the top of the head, and it is very difficult to construct a reasonable structure.

SUMMARY

An object of the present application is to overcome the defects of the low wearing firmness of the "I-shaped" headband assembly and the difficulty in the manufacturing, the complicated operation steps and the low wearing comfortableness of the "crown-shaped" headband assembly in the prior art.

In order to realize the above object, an aspect of the present application provides a headband assembly, wherein the headband assembly is of a planar structure in a spread and deployed state, and the headband assembly comprises a head-mounting part that is for clinging to and being worn on a head and connecting parts that are connected to two sides of the head-mounting part and are for connecting a respiratory mask; and the head-mounting part comprises an upper headband that is for clinging to a top of the head and has a preset width and a rear headband that is for clinging to a rear side of the head and is located under the upper headband, wherein the upper headband is of an arch structure whose concave faces the rear headband. Preferably, when the headband assembly is worn on the head, the upper headband having the preset width has a plurality of micro-surfaces, and centers of curvature of the plurality of micro-surfaces are in a same plane. The micro-surfaces used herein refer to that, when the headband assembly is worn on the head, when the headband assembly is exerted a certain force and the upper headband clings to the top of the head, the surface of the upper headband that clings to the top of the head is formed by a plurality of micro-surfaces.

The centers of curvature of the plurality of micro-surfaces are in the same plane, wherein the plane is a stable central plane that is formed after the headband assembly has been stably worn, and the stable central plane is a virtual plane. It can be understood that, because, in wearing, different persons have different comfortable wearing points, different persons have different stable central planes after they have worn the headband assembly, and the centers of curvature of the points of the upper headband are located in the stable central plane (in other words, as stated above, the upper headband has a plurality of micro-surfaces, and the centers of curvature of the plurality of micro-surfaces are in the same plane).

Preferably, the preset width of the upper headband is 16-36 mm.

Preferably, the upper headband is of a structure whose width is not constant.

Preferably, widths of two ends of the upper headband are greater than a width of a middle part of the upper headband. The width of the middle part is less, which can prevent the case in which, when the upper headband is bearing a force, a portion of the upper headband is excessively tightened and another portion is warped, thereby obtaining a higher integral conformability of the upper headband. Moreover, the widths of the two ends of the upper headband are greater, which can ensure a larger clinging area, to improve the stability of the headband assembly.

Preferably, a curvature radius of the arch structure gradually increases in extension directions from two ends to the middle part. Accordingly, the upper headband can further conform to the features of the head, to improve the conformability of the upper headband, thereby enhancing the stability of the headband assembly.

Preferably, the rear headband comprises a first band body and a second band body that are connected to two ends of the upper headband and a third band body that connects the first band body and the second band body; and the third band body comprises a third bottom band that connects one end of the first band body that is further away from the upper headband and one end of the second band body that is further away from the upper headband and/or a third middle band connected to a middle portion of the first band body and a middle portion of the second band body.

Preferably, the third bottom band is of an arch structure that faces the upper headband.

Preferably, each of the connecting parts comprises a side headband that is connected to one side of the upper headband and a bottom headband that is connected to one side of the rear headband.

Preferably, one end of the side headband that is further away from the upper headband and one end of the bottom headband that is further away from the rear headband are connected to form a connecting band.

According to another aspect of the present application, there is further provided a respiratory-mask system, wherein the respiratory-mask system comprises a respiratory mask and the headband assembly stated above, and the respiratory mask is connected to the connecting parts on two sides of the headband assembly.

In the headband assembly and respiratory-mask system according to the present application, by providing the headband assembly with the upper headband having the preset width and the arch structure, the headband assembly can enable the upper headband of the headband assembly to completely cling to the top of the head while having a planar structure in the spread state, and prevents the case in which a portion of the upper headband is excessively tightened to the top of the head and another portion of the upper headband is disengaged from the top of the head.

As compared with the I-shaped headband in the prior art, the headband assembly according to the present application can take into account the fixing of the head-top part, to improve the firmness when it is worn by a patient. Moreover, as compared with the crown-shaped headband in the prior art, the headband assembly according to the present application can realize the complete clinging to the top of the head while having a planar structure in the spread state, and, for realizing the same technical effects, the headband assembly according to the present application has a simpler manufacturing process, and greatly reduces the production cost.

According to another aspect of the present application, there is further provided another headband assembly, wherein the headband assembly is of a planar structure in a spread and deployed state, and the headband assembly comprises a head-mounting part that is for clinging to and being worn on a head and connecting parts that are connected to two sides of the head-mounting part and are for connecting a respiratory mask; and the head-mounting part comprises an upper headband that is for clinging to a top of the head and a rear headband that is for clinging to a rear side of the head and is located under the upper headband.

Preferably, when the headband assembly is worn on the head, the upper headband has a plurality of micro-surfaces, and centers of curvature of the plurality of micro-surfaces are in a same plane. The micro-surfaces used herein refer to that, when the headband assembly is worn on the head, when the headband assembly is exerted a certain force and the upper headband clings to the top of the head, the surface of the upper headband that clings to the top of the head is formed by a plurality of micro-surfaces.

The centers of curvature of the plurality of micro-surfaces are in the same plane, wherein the plane is a stable central plane that is formed after the headband assembly has been stably worn, and the stable central plane is a virtual plane. It can be understood that, because, in wearing, different persons have different comfortable wearing points, different persons have different stable central planes after they have worn the headband assembly, and the centers of curvature of the points of the upper headband are located in the stable central plane (in other words, as stated above, the upper headband has a plurality of micro-surfaces, and the centers of curvature of the plurality of micro-surfaces are in the same plane).

Preferably, the upper headband is of a structure whose width is not constant.

Preferably, widths of two ends of the upper headband are greater than a width of a middle part of the upper headband. The width of the middle part is less, which can prevent the case in which, when the upper headband is bearing a force, a portion of the upper headband is excessively tightened and another portion is warped, thereby obtaining a higher integral conformability of the upper headband. Moreover, the widths of the two ends of the upper headband are greater, which can ensure a larger clinging area, to improve the stability of the headband assembly.

Preferably, the rear headband comprises a first band body and a second band body that are connected to two ends of the upper headband and a third band body that connects the first band body and the second band body; and the third band body comprises a third bottom band that connects one end of the first band body that is further away from the upper headband and one end of the second band body that is further away from the upper headband and/or a third middle band connected to a middle portion of the first band body and a middle portion of the second band body.

Preferably, each of the connecting parts comprises a side headband that is connected to one side of the upper headband and a bottom headband that is connected to one side of the rear headband.

Preferably, one end of the side headband that is further away from the upper headband and one end of the bottom headband that is further away from the rear headband are connected to form a connecting band.

Preferably, the headband assembly is integrally formed.

Preferably, the upper headband is of a one-piece integral structure.

According to another aspect of the present application, there is further provided another respiratory-mask system, wherein the respiratory-mask system comprises a respiratory mask and the headband assembly stated above, and the respiratory mask is connected to the connecting parts on two sides of the headband assembly.

In the other headband assembly and respiratory-mask system according to the present application, by providing the headband assembly with the upper headband, the headband assembly can enable the upper headband of the headband assembly to completely cling to the top of the head while having a planar structure in the spread state, and prevents the case in which a portion of the upper headband is excessively tightened to the top of the head and another portion of the upper headband is disengaged from the top of the head.

As compared with the I-shaped headband in the prior art, the headband assembly according to the present application can take into account the fixing of the head-top part, to improve the firmness when it is worn by a patient. Moreover, as compared with the crown-shaped headband in the prior art, the headband assembly according to the present application can realize the complete clinging to the top of the head while having a planar structure in the spread state, and, for realizing the same technical effects, the headband assembly according to the present application has a simpler manufacturing process, and greatly reduces the production cost.

According to another aspect of the present application, there is further provided another headband assembly, wherein the headband assembly comprises a head-mounting part that is for clinging to and being worn on a head and connecting parts that are connected to two sides of the head-mounting part and are for connecting a respiratory mask, and the head-mounting part comprises an upper headband that is for clinging to a top of the head and a rear headband that is for clinging to a rear side of the head and is located under the upper headband, wherein the upper headband and the connecting parts are of a planar structure in a spread and deployed state.

Preferably, when the headband assembly is worn on the head, the upper headband has a plurality of micro-surfaces, and centers of curvature of the plurality of micro-surfaces are in a same plane. The micro-surfaces used herein refer to that, when the headband assembly is worn on the head, when the headband assembly is exerted a certain force and the upper headband clings to the top of the head, the surface of the upper headband that clings to the top of the head is formed by a plurality of micro-surfaces.

The centers of curvature of the plurality of micro-surfaces are in the same plane, wherein the plane is a stable central plane that is formed after the headband assembly has been stably worn, and the stable central plane is a virtual plane. It can be understood that, because, in wearing, different persons have different comfortable wearing points, different persons have different stable central planes after they have worn the headband assembly, and the centers of curvature of the points of the upper headband are located in the stable central plane (in other words, as stated above, the upper headband has a plurality of micro-surfaces, and the centers of curvature of the plurality of micro-surfaces are in the same plane).

Preferably, the upper headband is of a structure whose width is not constant.

Preferably, widths of two ends of the upper headband are greater than a width of a middle part of the upper headband. The width of the middle part is less, which can prevent the case in which, when the upper headband is bearing a force, a portion of the upper headband is excessively tightened and another portion is warped, thereby obtaining a higher integral conformability of the upper headband. Moreover, the widths of the two ends of the upper headband are greater, which can ensure a larger clinging area, to improve the stability of the headband assembly.

Preferably, the rear headband comprises a first band body and a second band body that are connected to two ends of the upper headband and a third band body that connects the first band body and the second band body; and the third band body comprises a third bottom band that connects one end of the first band body that is further away from the upper headband and one end of the second band body that is further away from the upper headband and/or a third middle band connected to a middle portion of the first band body and a middle portion of the second band body.

Preferably, each of the connecting parts comprises a side headband that is connected to one side of the upper headband and a bottom headband that is connected to one side of the rear headband.

Preferably, one end of the side headband that is further away from the upper headband and one end of the bottom headband that is further away from the rear headband are connected to form a connecting band.

Preferably, the headband assembly is integrally formed.

Preferably, the upper headband is of a one-piece integral structure.

According to another aspect of the present application, there is further provided another respiratory-mask system, wherein the respiratory-mask system comprises a respiratory mask and the headband assembly stated above, and the respiratory mask is connected to the connecting parts on two sides of the headband assembly.

In the other headband assembly and respiratory-mask system according to the present application, by providing the headband assembly with the upper headband, the headband assembly can enable the upper headband of the headband assembly to completely cling to the top of the head while having a planar structure in the spread state, and prevents the case in which a portion of the upper headband is excessively tightened to the top of the head and another portion of the upper headband is disengaged from the top of the head.

As compared with the I-shaped headband in the prior art, the headband assembly according to the present application can take into account the fixing of the head-top part, to improve the firmness when it is worn by a patient. Moreover, as compared with the crown-shaped headband in the prior art, the headband assembly according to the present application can realize the complete clinging to the top of the head while having a planar structure in the spread state, and, for realizing the same technical effects, the headband assembly according to the present application has a simpler manufacturing process, and greatly reduces the production cost.

The above description is merely a summary of the technical solutions of the present application. In order to more clearly know the elements of the present application to enable the implementation according to the contents of the description, and in order to make the above and other purposes, features and advantages of the present application more apparent and understandable, the particular embodiments of the present application are provided below.

BRIEF DESCRIPTION OF THE DRAWINGS

In order to more clearly illustrate the technical solutions of the embodiments of the present application or the prior art, the figures that are required to describe the embodiments or the prior art will be briefly introduced below. Apparently, the figures that are described below are embodiments of the present application, and a person skilled in the art can obtain other figures according to these figures without paying creative work.

DESCRIPTION OF THE REFERENCE NUMBERS

1—head-mounting part; 11—upper headband; 111—lengthened parts; 12—rear headband; 121—first band body; 122—second band body; 123—third band body; 1231—third bottom band; 1232—third middle band; 2—connecting parts; 21—side headbands; 211—first positions; 212—second positions; and 22—bottom headbands.

DETAILED DESCRIPTION

In order to make the objects, the technical solutions and the advantages of the embodiments of the present application clearer, the technical solutions of the embodiments of the present application will be clearly and completely described below with reference to the drawings of the embodiments of the present application. Apparently, the described embodiments are merely certain embodiments of the present application, rather than all of the embodiments. All of the other embodiments that a person skilled in the art obtains on the basis of the embodiments of the present application without paying creative work fall within the protection scope of the present application.

Figure 1:
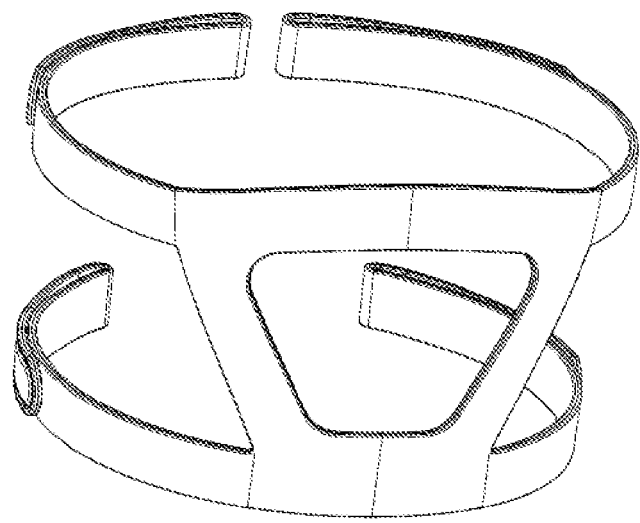
FIG. 1 is a schematic structural diagram of the "I-shaped" headband assembly in the prior art.
Figure 2:
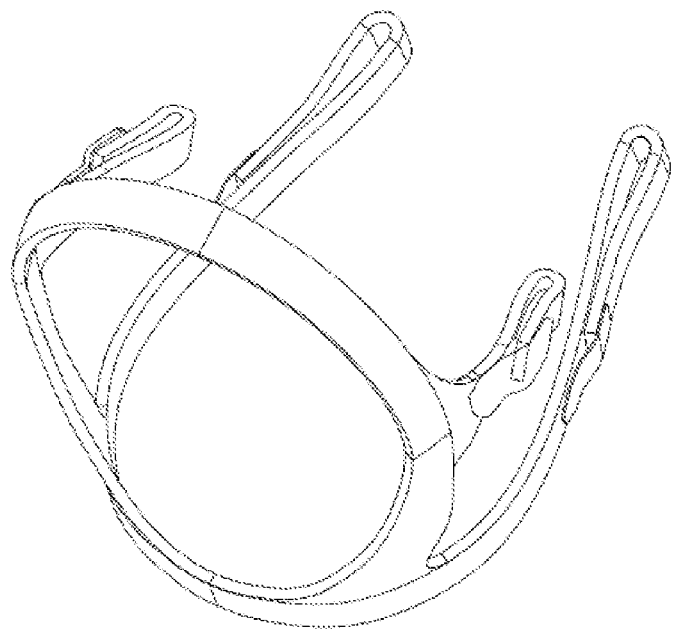
FIG. 2 is a schematic structural diagram of the "crown-shaped" headband assembly in the prior art.
Figure 3:
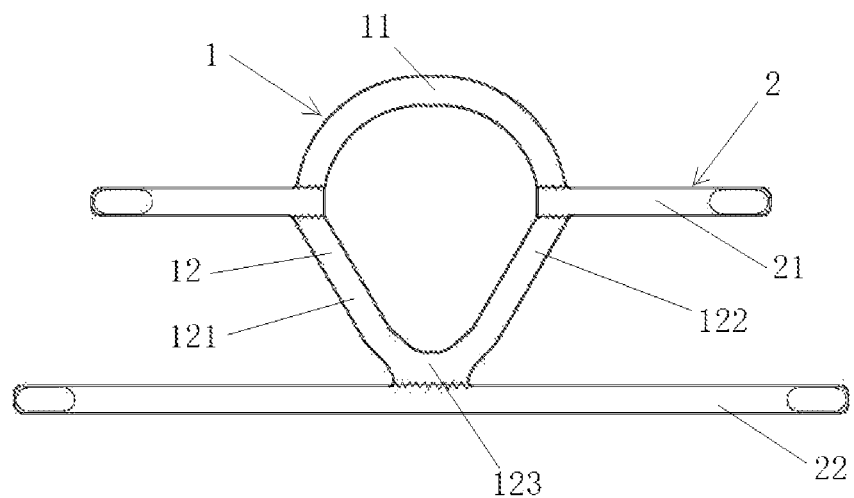
FIG. 3 is a schematic structural diagram of the headband assembly according to an embodiment of the present application.

The present application provides a headband assembly. As shown in FIG. 3, the headband assembly is of a planar structure in a spread and deployed state. The headband assembly comprises a head-mounting part 1 that is for clinging to the head and connecting parts 2 that are connected to the two sides of the head-mounting part 1 and are for connecting a respiratory mask. The head-mounting part 1 of the headband assembly comprises an upper headband 11 that is for clinging to a top of the head and a rear headband 12 that is for clinging to a rear side of the head and is located under the upper headband 11. The rear headband 12 is connected to the two ends of the upper headband 11. The upper headband 11 is of an arch structure whose concave faces the rear headband 12.

In the headband assembly according to the present application, by providing the upper headband having the preset width and the arch structure, the headband assembly can enable the upper headband of the headband assembly to completely cling to the top of the head while having a planar structure in the spread and deployed state, and prevents the case in which a portion of the upper headband is excessively tightened to the top of the head and another portion of the upper headband is disengaged from the top of the head. As compared with the I-shaped headband in the prior art, the headband assembly according to the present application can take into account the fixing of the head-top part, to improve the firmness when it is worn by a patient. Moreover, as compared with the crown-shaped headband in the prior art, the headband assembly according to the present application can realize the complete clinging to the top of the head while having a planar structure in the spread state, and, for realizing the same technical effects, the headband assembly according to the present application has a simpler manufacturing process, and greatly reduces the production cost.

When the headband assembly is worn on the head, the upper headband 11 having the preset width has a plurality of micro-surfaces, and the centers of curvature of the plurality of micro-surfaces are in the same plane. The micro-surfaces used herein refer to that, when the headband assembly is worn on the head, when the headband assembly is exerted a certain force and the upper headband 11 clings to the top of the head, the surface of the upper headband 11 that clings to the top of the head is formed by a plurality of micro-surfaces.

The centers of curvature of the plurality of micro-surfaces are in the same plane, wherein the plane is a stable central plane that is formed after the headband assembly has been stably worn, and the stable central plane is a virtual plane. It can be understood that, because, in wearing, different persons have different comfortable wearing points, different persons have different stable central planes after they have worn the headband assembly, and the centers of curvature of the points of the upper headband 11 are located in the stable central plane (in other words, as stated above, the upper headband 11 has a plurality of micro-surfaces, and the centers of curvature of the plurality of micro-surfaces are in the same plane).

The preset width of the upper headband 11 may be obtained from the relation between, when the headband assembly is worn on the head, the curvature radiuses of the micro-surfaces of the upper headband 11 and the curvature radiuses of the top of the head. Particularly, the positions of the top of the head that cling to the upper headband 11 have first micro-surfaces, and the curvature radiuses of the first micro-surfaces are the first radiuses. The upper headband 11 has second micro-surfaces that correspond to the first micro-surfaces, and the curvature radiuses of the second micro-surfaces are the second radiuses. When the structures and the areas of the first micro-surfaces and the second micro-surfaces become increasingly consistent, the ideal values of the second radiuses can be obtained, whereby the upper headband 11 and the top of the head can cling to the maximum extent. In this case, the curvature radiuses of the first micro-surfaces and the second micro-surfaces are in the same plane (i.e., the stable central plane).

Figure 15:
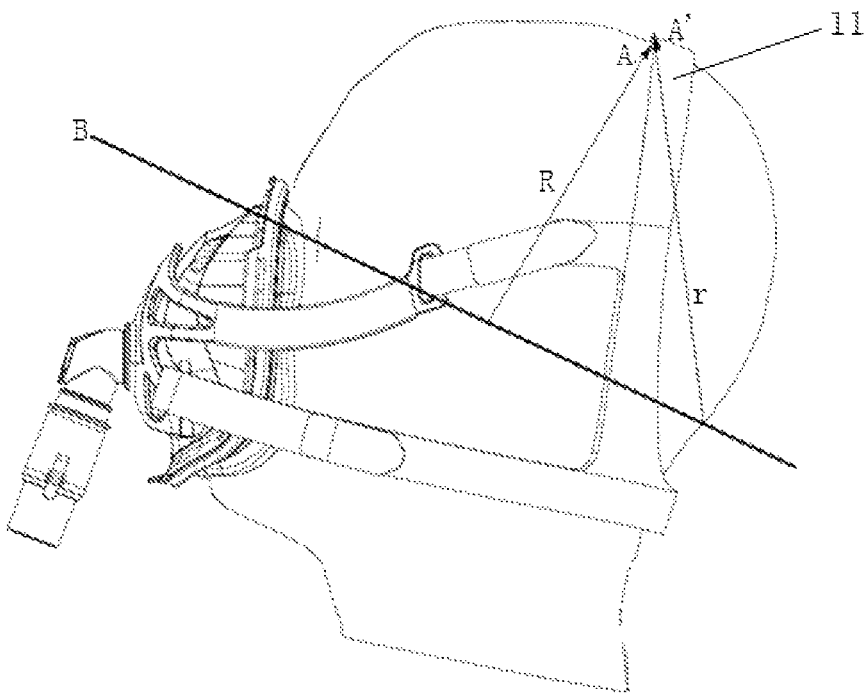
FIG. 15 is a schematic structural diagram of the headband assembly according to the present application when it is worn on a head.
Figure 16:
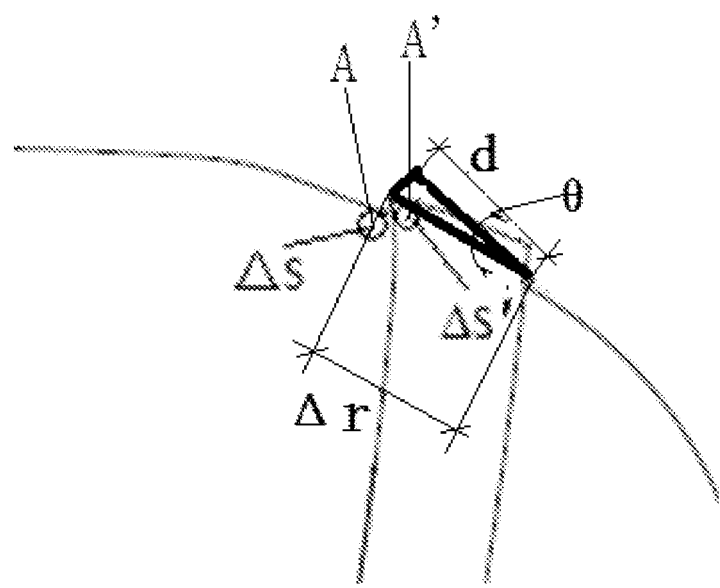
FIG. 16 is a partially enlarged schematic diagram of the structure in FIG. 15.

Particularly, as shown in FIGS. 15 and 16, the upper headband clings to the top of the head of the wearer. Taking the point A of the top of the head as the example, a microscopic small micro-surface ΔS is formed around the point A, and R is the curvature radius of the micro-surface ΔS, which is the distance from the point A to the center of curvature of the micro-surface ΔS. The rest can be done in the same manner, and accordingly the positions of the top of the head that cling to the upper headband 11 have a plurality of micro-surfaces ΔS, wherein those micro-surfaces ΔS form the top of the head. The upper headband 11 has a point A' corresponding to the point A. A microscopic small micro-surface ΔS' is formed around the point A', and r is the curvature radius of the micro-surface ΔS', which is the distance from the point A' to the center of curvature of the micro-surface ΔS'. A plurality of the micro-surfaces ΔS' can form the surface of the upper headband 11 that clings to the top of the head.

When the space structure of the planes ΔS' and the space structure of the planes ΔS infinitely approaches being the same, the upper headband 11 that they form can fully cling to the top of the head in use. When the space structure of the ΔS' infinitely approaches the space structure of the ΔS, it can be obtained that the relation between r and R is:

$$r=kR+m,$$

wherein k is a parameter that is related to the design structure, the positioning points and the material characteristics of the headband, and m is a compensation value.

Generally, the material of the headband assembly has a certain elasticity, which allows the space structure of the ΔS' and the space structure of the ΔS to have a deviation within a predetermined range, to obtain the deviation range Δr of r. It is set that, in the spread and deployed state of the upper headband, the width at the point A' is d, and it is obtained that:

$$d=k'\Delta r \cos\theta+m',$$

wherein k' is a correction parameter, θ is the angle between Δr and d, and m' is a correction value.

From the above formulas, the maximum width value of the upper headband 11 can be obtained, which can ensure the complete clinging between the upper headband and the top of the head, and prevent the case in which a portion of the upper headband is excessively tightened to the top of the head and another portion of the upper headband is disengaged from the top of the head. Thereby obtaining a good firmness of the entire headband assembly.

Preferably, the preset width of the upper headband 11 is 16-36 mm. When the width value of the upper headband 11 is small, it has a good conformability with the top of the head, but the stability is poor and the headband easily gets loose. When the width value is large, it has a good stability, but the conformability is poor, which reduces the comfortableness of the wearer. According to the demands, the headband width of the upper headband 11 may be determined according to the obtained widths d of the multiple points. For example, the width of an upper headband having a constant width may be obtained from the obtained width average value, and an upper headband having variable curvatures may be designed according to the variation of the width. It can be understood that, in order to better realize the firm clinging between the upper headband and the top of the head of the wearer, more detailed calculus algorithms or other algorithms may be used to further accurately calculate to obtain the width of the upper headband.

Figure 4:
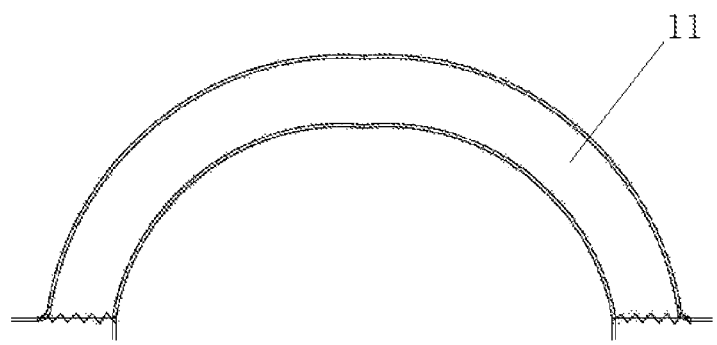
FIG. 4 is a schematic structural diagram illustrating the upper headband of the headband assembly (the upper headband is of a structure whose width is constant)
Figure 5:
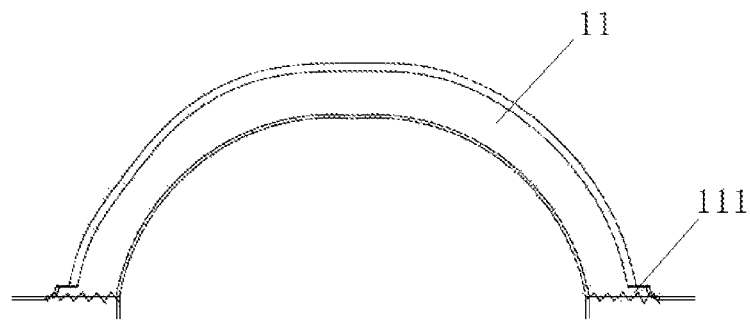
FIG. 5 is a schematic structural diagram illustrating the upper headband of the headband assembly (the upper headband is of a structure whose width is not constant)

The width value of the upper headband 11 may be determined particularly according to the properties of the different elastic materials for manufacturing the upper headband 11, thereby realizing multiple designs of planar or crown headbands. In addition, according to the properties of the materials and so on, the upper headband 11 may be designed to be a band-shaped body of a constant width (shown in FIG. 4) or a band-shaped body whose width is not constant (shown in FIG. 5). By designing the upper headband 11 to be a structure whose width is not constant, the usage performance of the planar headband can be optimized.

Preferably, the widths of the two ends of the upper headband 11 are greater than the width of the middle part of the upper headband 11. The width of the middle part is less, which can prevent the case in which, when the upper headband is bearing a force, a portion of the upper headband is excessively tightened and another portion is warped, thereby obtaining a higher integral conformability of the upper headband. Moreover, the widths of the two ends of the upper headband are greater, which can ensure a larger clinging area, to improve the stability of the headband assembly.

Preferably, the curvature radius of the arch structure of the upper headband 11 gradually increases in the extension directions from the two ends to the middle part. Accordingly, the upper headband 11 can further conform to the features of the head, to improve the conformability of the upper headband, thereby enhancing the stability of the headband assembly.

The characteristics such as the widths and the curvature radiuses of the positions of the upper headband 11 may be particularly set according to the material characteristics, the head features and so on, to enable it to better cling to the head.

It can also be understood that the upper headband 11 may be formed by the splicing, cutting or stamping of the same one elastic material, and the upper headband may be formed by the splicing of different elastic materials.

In the headband assembly, besides the clinging of the upper headband 11 to the top of the head, the rear headband 12 is required to cling to the rear side of the head, whereby, when the connecting parts pull the head-mounting part 1 forwardly, the headband assembly can be firmly worn. The rear headband 12 may have multiple structures and forms.

In some embodiments, as shown in FIGS. 3, 7, 9-12 and 14, the rear headband 12 and the upper headband 11 form a non-detachable closed-loop structure. To wear it, the user is merely required to connect the connecting parts with the headband assembly, which reduces the steps of the operation of the user when the rear headband or the upper headband is detachably connected or they are detachably interconnected, and overcomes the problem of the low wearing comfortableness for the user at the connections.

Figure 12:
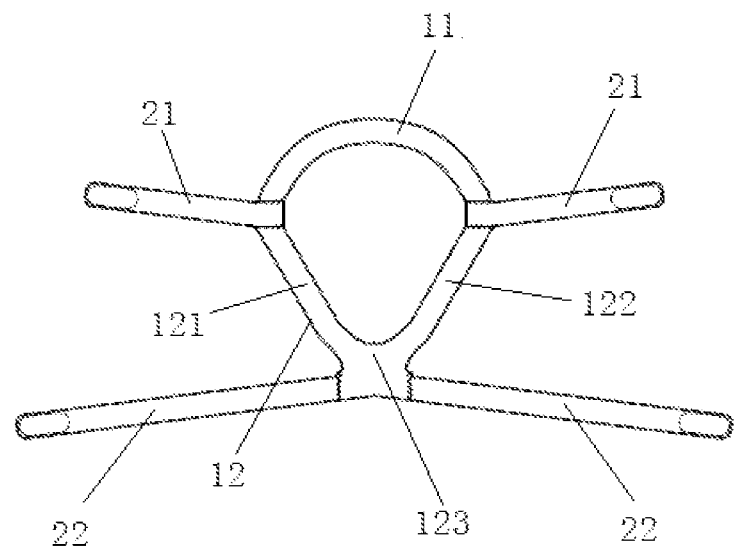
FIG. 12 is a schematic structural diagram of the headband assembly according to still another embodiment of the present application.

Particularly, as shown in FIGS. 3 and 12, the rear headband 12 comprises a first band body 121 and a second band body 122 that are connected to the two ends of the upper headband 11 and a third band body 123 that connects the first band body 121 and the second band body 122.

In some embodiments, the third band body 123 comprises a third bottom band 1231 that connects one end of the first band body 121 that is further away from the upper headband 11 and one end of the second band body 122 that is further away from the upper headband 11. Preferably, the third bottom band 1231 is of an arch structure that faces the upper headband 11, wherein the facing refers to that the side of the arch structure of the upper headband 11 that is inwardly concave and the side of the arch structure of the third bottom band 1231 that is inwardly concave face each other.

Figure 14:
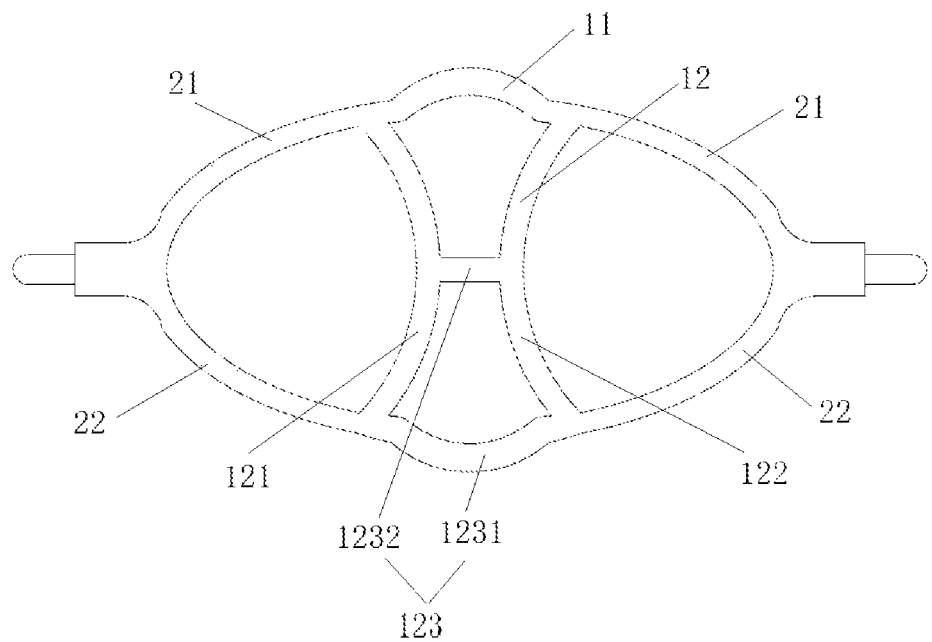
FIG. 14 is a schematic structural diagram of the headband assembly according to still another embodiment of the present application (the headband assembly is of the two-point connection mode)

In another embodiment, as shown in FIG. 14, the third band body 123 may also comprise a third middle band 1232 that is connected to the middle portion of the first band body 121 and the middle portion of the second band body 122.

In the embodiments shown in FIGS. 3, 7 and 9-12, the ends of the first band body 121 and the second band body 122 that are further away from the upper headband 11 are inclined toward each other and are connected. Such a configuration of the rear headband 12 facilitates to form a smooth contact interface between the headband and the head, and the structure of the wider top and the narrower bottom facilitates the stability of the wearing.

More preferably, the included angle between the first band body 121 and the second band body 122 is 20°-70°.

Certainly, the first band body 121 and the second band body 122 may have alternations according to the detailed designs. For example, in the embodiment shown in FIG. 13, the first band body 121 and the second band body 122 form arc-shaped structures whose middle portions expand outwardly. Moreover, in the embodiment shown in FIG. 14, the middle portions of the first band body 121 and the second band body 122 are closer to each other, and the two ends are further away from each other, whereby the middle portions are suitable for connecting the third middle band 1232.

In the headband assembly, each of the connecting parts 2 comprises a side headband 21 that is connected to one side of the upper headband 11 and a bottom headband 22 that is connected to one side of the rear headband 12.

The side headbands 21 on the two sides are individually connected to the connection points of the upper headband 11 and the rear headband 12; in other words, the three are connected together. The smooth connection of the upper headband 11, the side headbands 21 and the rear headband 12 forms the smooth contact interface between the headband and the head. Two positioning points on the two sides of the head are determined, and the positioning points facilitate to more firmly wear the respiratory-mask system.

In the technical solutions according to the present application, the side headbands 21 on the two sides of the upper headband 11 and the bottom headbands 22 on the two sides of the rear headband 12 may be individually provided with a connection structure for connecting the respiratory mask (not shown in the drawings), which is the "four-point-type" connection mode (connection with the respiratory mask via four connection points).

Figure 7:
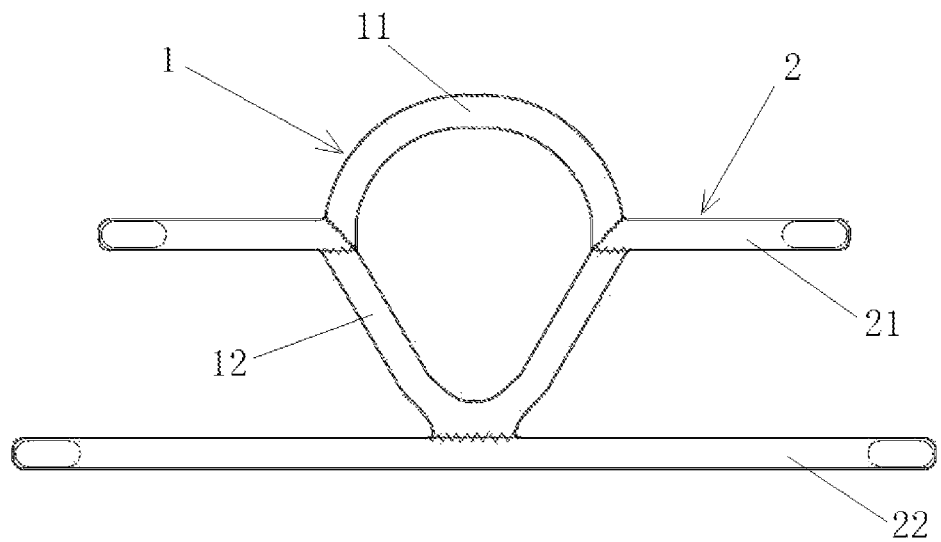
FIG. 7 is a schematic structural diagram of the headband assembly according to another embodiment of the present application.

In the "four-point-type" connection mode, preferably, the side headbands 21 and the bottom headbands 22 are parallel to each other in the deployed state, as shown in FIGS. 3 and 7. Certainly, the side headbands 21 and the bottom headbands 22 may also be set to be not parallel (for example, in FIG. 11 the side headbands 21 and the bottom headbands 22 are inclined toward each other, and in FIG. 12 the side headbands 21 and the bottom headbands 22 are inclined away from each other), and by adjusting particularly the side headbands 21 and the bottom headbands 22 according to the design of the head-mounting part 1 or other particular conditions, the side headbands 21 and the bottom headbands 22 can cling to the head better when connecting the respiratory mask.

Figure 13:
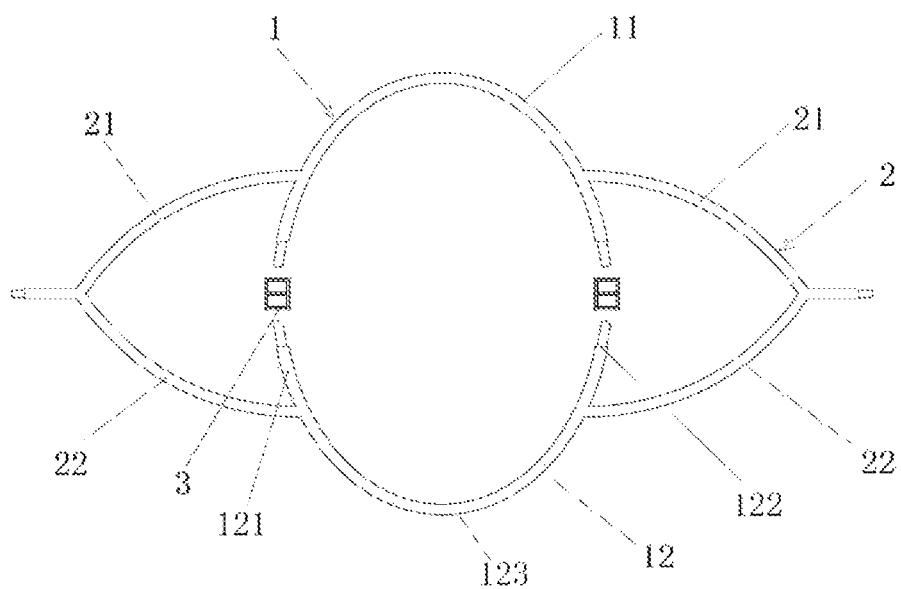
FIG. 13 is a schematic structural diagram of the headband assembly according to still another embodiment of the present application (the headband assembly is of the two-point connection mode)

In addition, on each of the sides of the head-mounting part 1, the ends of the side headbands 21 and the bottom headbands 22 that are further away from the head-mounting part 1 may be connected to each other to form a connecting band, as shown in FIGS. 13 and 14. Connecting structures for connecting the respiratory mask are provided at the ends that are connected with each other (as the embodiments shown in FIGS. 13 and 14), which is the "two-point-type" connection mode (connection with the respiratory mask via two connection points). Such a two-point-type headband can pass through the top of the head of the user, to enable firm wearing. The laterally symmetrical structure in which the rear headband clings to the head back further improves the conformability and the firmness between the head-mounting part and the head.

It can also be seen from the structures shown in FIGS. 13 and 14 that the headband assembly is of a symmetrical structure. In other words, the upper part and the lower part of the head-mounting part 1 may be reversed upside-down to wear, and it is not required to distinguish the upper part and the lower part, which makes the wearing more convenient.

Here, it should also be noted that a person skilled in the art can understand that the head-mounting part 1 of the headband assembly may also have other shapes according to the demands, to satisfy the various demands of consumers on the styles of the headband, which is not described in detail here.

In order to facilitate to manufacture the planar headband assembly, preferably, the upper headband 11, the rear headband 12, the side headbands 21 and the bottom headbands 22 may be connected together by splicing. In other words, the headband assembly will be cut into the component parts of the flat planes, which are then spliced (for example, spliced by stitching, welding, pressure welding and so on). That can save the material, and reduce the difficulty in the manufacturing.

Preferably, as shown in FIG. 3, on each side of the head-mounting part 1, the upper headband 11 and the rear headband 12 are spliced to the edges of the two opposite sides of the side headband 22 on that side.

Figure 6:
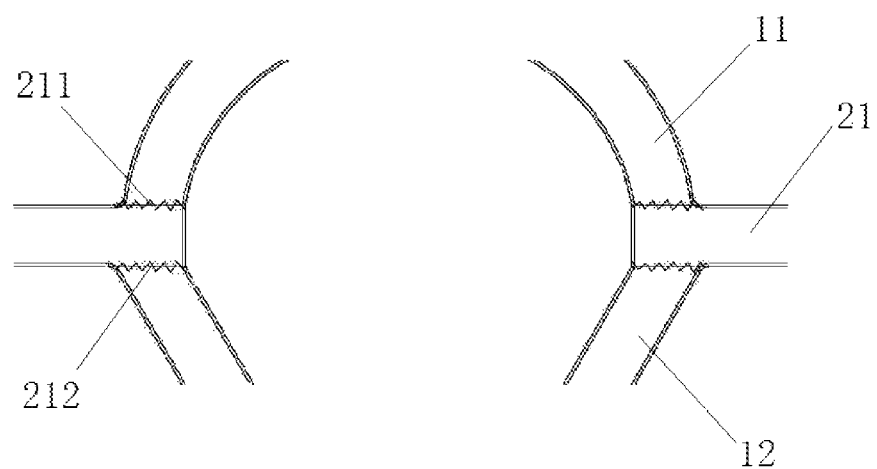
FIG. 6 is a schematic structural diagram illustrating the connecting positions of the headband assembly shown in FIG. 3.

Further, particularly, as shown in FIGS. 3 and 6, a first position 211 of the side headband 21 that is spliced to the upper headband 11 and a second position 212 of the side headband 21 that is spliced to the rear headband 12 are parallel. In other words, the first position 211 and the second position 212 are parallel to each other, and when the side headband 21 is exerted a pulling force, the force bearing point is located at a position of the side headband 21 that is located between the first position 211 and the second position 212. Such a splicing mode can facilitate the headband assembly to cling to the head when exerted a force, and has a good fine-tuning effect, whereby no tilting of some positions happens when the side headband 21 is pulled and bears force. In addition, in order to enhance the connection, a lengthened part 111 may be provided at the position of the upper headband 11 that is connected to the side headband 21, to increase the length of the upper headband 11 that is connected to the side headband 21, thereby enabling the connection to be more firm.

Figure 8:
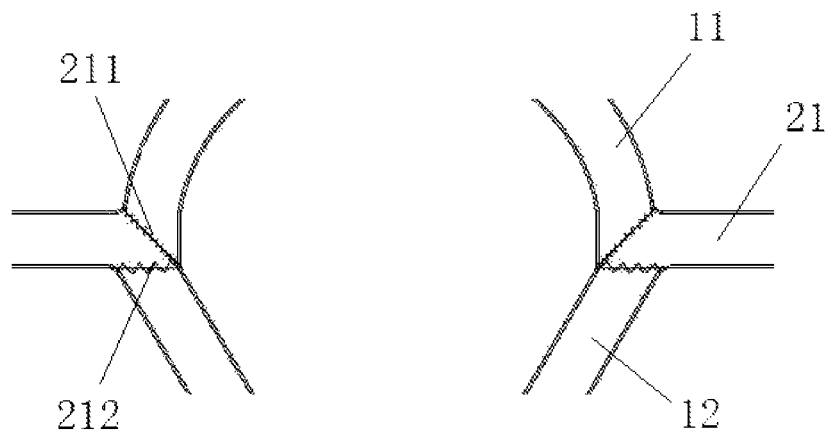
FIG. 8 is a schematic structural diagram illustrating the connecting positions of the headband assembly shown in FIG. 7.

Alternatively, as shown in FIG. 7 or 8, the first position 211 of the side headband 21 that is spliced to the upper headband 11 is inclined with respect to the second position 212 of the side headband 21 that is spliced to the rear headband 12 to form a bevel structure. Correspondingly, the end of the upper headband 11 that is connected to the side headband 21 is configured to be a bevel structure that cooperates with the bevel structure. Accordingly, when the side headband 21 is pulled, the sharp corner of the bevel structure is the force bearing point. Such a splicing mode can also enable the headband assembly to cling to the head when exerted a force.

The splicing between the bottom headbands 22 and the rear headband 12 may be as shown in FIG. 3, wherein the bottom headbands 22 on the two sides are formed by splicing the entire band-shaped body to the lower end of the rear headband 12 and extending toward the two sides.

Figure 9:
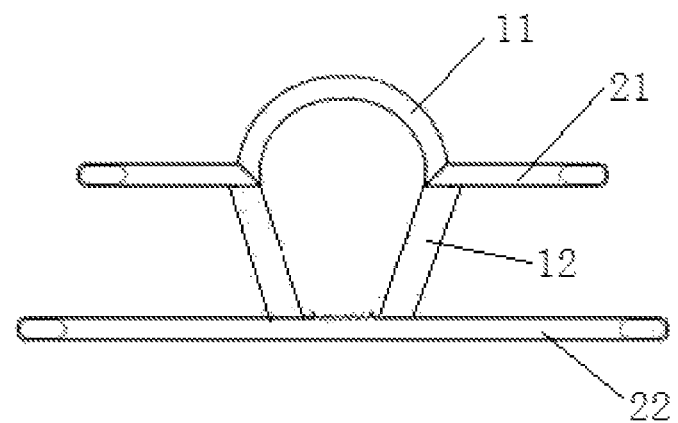
FIG. 9 is a schematic structural diagram of the headband assembly according to yet another embodiment of the present application.

Particularly, as shown in FIG. 3, the ends of the first band body 121 and the second band body 122 of the rear headband 12 that are further away from the upper headband 11 are connected with each other, and then are spliced to the middle position of the entire band-shaped body to form the bottom headbands 22 located on the two sides. Optionally, as shown in FIG. 9, the first band body 121 and the second band body 122 of the rear headband 12 are individually connected with the band-shaped body, and the parts of the band-shaped body that extend away from the rear headband 12 individually form the bottom headbands 22.

Figure 10:
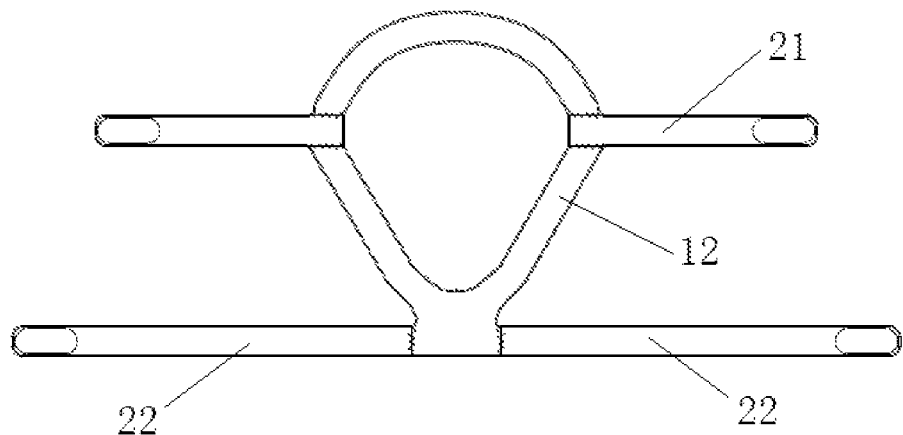
FIG. 10 is a schematic structural diagram of the headband assembly according to still another embodiment of the present application.
Figure 11:
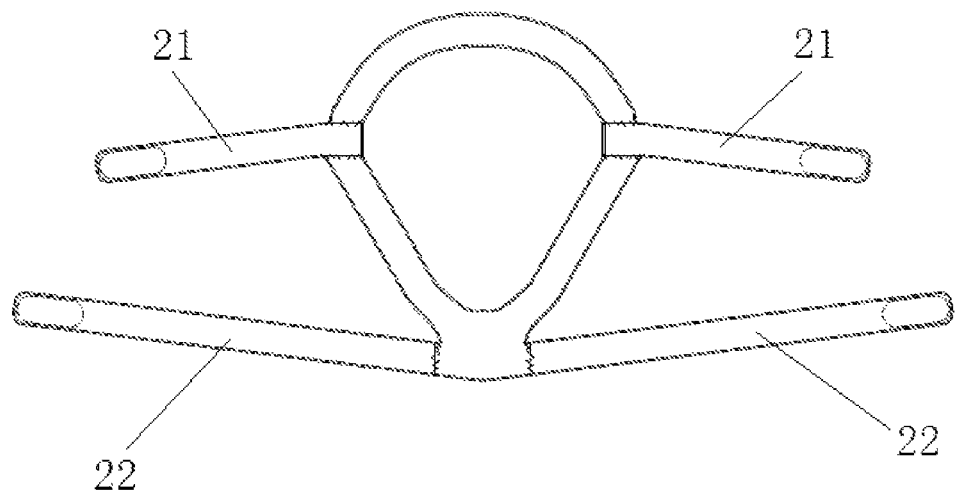
FIG. 11 is a schematic structural diagram of the headband assembly according to still another embodiment of the present application.

Certainly, the bottom headbands 22 may also be configured as two parts, and the two parts are on the two sides of the rear headband 12 and connected with the lower ends of the bottom headbands 22 (as shown in FIGS. 10 and 11).

Certainly, the spliced structure is not limited to those stated above, and the spliced structures stated above are preferable embodiments that enable the headband assembly to cling to the head better.

It should also be understood that the headband assembly may be formed by splicing, but it may also be integrally formed, i.e., cut entirely from a planar material or integrally formed by another mode. However, the splicing mode, as compared with the integrally forming mode, saves the material, has a simpler manufacturing process, saves the cost and improves the production efficiency. In addition, the connection may also be via snap fitting by using clips (for example, as shown in FIG. 13, the first band body 121 and the second band body 122 of the rear headband 12 are individually provided with a clip 3, and are snap-fitted together via the clips 3).

According to another aspect of the present application, there is further provided a respiratory-mask system, wherein the respiratory-mask system comprises a respiratory mask and the headband assembly stated above, and the respiratory mask is connected to the connecting parts 2 on the two sides of the headband assembly. The respiratory-mask system employs the headband assembly stated above, which can enable firm wearing, reduce the manufacturing cost and improve the manufacturing efficiency.

What is claimed is:

1. A headband assembly, wherein the headband assembly is of a planar structure where the headband assembly is entirely in a same plane in a spread and deployed state, and the headband assembly comprises a head-mounting part that is for clinging to and being worn on a head and connecting parts that are connected to two sides of the head-mounting part and are for connecting a respiratory mask; and the head-mounting part comprises an upper headband that is for clinging to a top of the head and has a preset width and a rear headband that is for clinging to a rear side of the head and is located under the upper headband, wherein the upper headband is of an arch structure whose concave faces the rear headband;

wherein each of the connecting parts comprises a side headband that is connected to one side of the upper headband and a bottom headband that is connected to one side of the rear headband; and wherein the side headbands and the bottom headbands are inclined toward each other;

when the headband assembly is worn on the head, the upper headband having the preset width has a plurality of micro-surfaces, and centers of curvature of the plurality of micro-surfaces are in a same plane.

2. The headband assembly according to claim 1, wherein the preset width of the upper headband is 16-36 mm.

3. The headband assembly according to claim 2, wherein the upper headband is of a structure whose width is not constant.

4. The headband assembly according to claim 3, wherein widths of two ends of the upper headband are greater than a width of a middle part of the upper headband.

5. The headband assembly according to claim 1, wherein the rear headband comprises a first band body and a second band body that are connected to two ends of the upper headband and a third band body that connects the first band body and the second band body; and the third band body comprises a third bottom band that connects one end of the first band body that is further away from the upper headband and one end of the second band body that is further away from the upper headband and/or a third middle band connected to a middle portion of the first band body and a middle portion of the second band body.

6. The headband assembly according to claim 5, wherein the third bottom band is of an arch structure that faces the upper headband.

7. The headband assembly according to claim 1, wherein one end of the side headband that is further away from the upper headband and one end of the bottom headband that is further away from the rear headband are connected to form a connecting band.

8. A respiratory-mask system, wherein the respiratory-mask system comprises a respiratory mask and the headband assembly according to claim 1, and the respiratory mask is connected to the connecting parts on two sides of the headband assembly.

9. The headband assembly according to claim 1, wherein a curvature radius of the arch structure gradually increases in extension directions from two ends to a middle part of the upper headband.

* * * * *